United States Patent [19]

Liu

[11] Patent Number: 5,700,656
[45] Date of Patent: Dec. 23, 1997

[54] SILVER STAIN FOR COLLAGEN MATRIX FROM PARAFFIN EMBEDDED TISSUE

[75] Inventor: Si-kwang Liu, Jamaica Estates, N.Y.

[73] Assignee: Pig Research Institute, Taiwan, Maioli, Taiwan

[21] Appl. No.: 449,910

[22] Filed: May 25, 1995

[51] Int. Cl.⁶ .................................................. C12Q 1/08
[52] U.S. Cl. .................................................. 435/40.52
[58] Field of Search .................................. 435/40.52

[56] References Cited

PUBLICATIONS

Novotny E. et al., "A Modification of the Glees Silver Impregnation for Normal and Degenerating Nervous Tissue", Stain Tech. 49(5):273–80 (1974).

Moos T et al., Histochemistry 99(6):471–5 (1993).

Brown GG. et al., Stain Technology 44(5):247–9 (1969).

Abstract 151 Interstitial Connective Tissue Abnormalities in Feline Cardiomyopathies, Si–Kwang Liu et al. United States & Canadian Academy of Pathology Annual Meeting, San Francisco Mar. 12–18, 1994.

*Primary Examiner*—Sandra E. Saucier
*Attorney, Agent, or Firm*—Neal O. Willmann

[57] ABSTRACT

A technique for staining and preparing mammalian tissue for examination and study is disclosed. The technique features a fixed tissue that is embedded with paraffin to facilitate the cutting of uniformly thin sections and the penetration of a silver stain into the interstices of the collagen matrix. In particular, a 25–30 micron thick slice of cardiac tissue is silver stained and examined for cardiomyopathies.

6 Claims, No Drawings

SILVER STAIN FOR COLLAGEN MATRIX FROM PARAFFIN EMBEDDED TISSUE

BACKGROUND OF THE INVENTION

The subject matter of this disclosure relates, in general, to a method of identifying disease conditions in mammals by examining mammalian tissue to determine the abnormal quantity and orientation of collagen matrix in their organs. It has been observed that matrix increase and disorientation are evident in human and animal organs when various diseases are present. The microscopic examination of the collagen matrix of mammalian tissues, leading to the possible diagnosis of a disease condition, is performed using a novel procedure that impregnates a paraffin-embedded tissue with a silver stain. For example, if a cardiac disease condition exists, the silver impregnation will highlight and permit the detection of marked increases in perimysial coils, pericellular weaves and cell to cell struts in the myocardium. Matrix disorientation is also evident in the stained hypertrophic heart muscle.

DESCRIPTION OF THE PRIOR ART

It has been previously disclosed by Liu et al. at the International Academy of Pathology, Annual Meeting, San Francisco, Calif., Mar. 12-18, 1994 that silver impregnation stain can be used to identify perimysial coils, pericellular weave fibers and cell to cell struts in cardiomyopathic hearts, but the procedure utilized by Liu et al. was difficult to perform. Because of a rigidity in the frozen formalin fixed tissue, a uniformly thin section was difficult, and sometimes impossible, to cut and an effective penetration of the stain was unpredictable. It should be apparent that if the tissue section is too thick and irregular, the staining impregnation process is haphazard and a thorough and reliable examination of the matrix is compromised. The method disclosed herein employs a paraffin embedding technique that maintains the integrity of the tissue and permits a uniformly thinner section to be cut, stained and examined.

SUMMARY OF THE INVENTION

The disclosed method demonstrates a procedure for diagnosing disease conditions such as cardiovascular dysfunction in mammals. The procedure comprises the sequential steps of: fixing a tissue specimen, washing the specimen in water to remove any excess fixative, dehydrating the washed specimen in an alcohol, clearing the dehydrated specimen in an aromatic organic compound, embedding the cleared specimen with a melted paraffin, allowing the embedded section to cool and form a paraffin block, cutting a histological section no greater than 30 microns from the paraffin block, deparaffinizing the tissue section, clearing the deparaffinized section in an aromatic organic compound, rehydrating the cleared section in an alcohol, staining the rehydrated section with a silver solution, dehydrating the stained section in an alcohol, clearing the dehydrated stained section with an aromatic organic compound, mounting the cleared section and examining the stained section, under a microscope, to detect any connective tissue abnormalities.

DESCRIPTION OF PREFERRED EMBODIMENTS

Hypertrophic cardiomyopathy (HCM), a major cause of sudden death in humans and animals, is a primary cardiac disease in which the most characteristic morphological features are a hypertrophied, nondilated left ventrical and a myocardium typically showing bizarre and disorganized cellular architecture, abnormally small intramural coronary arteries and increased amounts of matrix or replacement fibrosis.

The collagen matrix of cardiac tissue consists of pericellular, interstitial and fascicular connective tissues that serve as a skeletal framework for the myocardium. This matrix contributes to normal cardiac function and, if altered, cardiac dysfunction may result. It matters little whether irregularities in the matrix result from or contribute to the dysfunction or disease condition, but it is important from a pathophysiologist's point of view to be able to model and study a disease condition by simply examining matrix tissues for abnormal structural characteristics, studying pathophysiologic and clinical aspects and determining the effects of chemical agents on the matrix irregularities. Unfortunately, the matrix is relatively invisible. Even when stained with traditional or even special stains such as Masson's trichrome or Verhoeff's Elastin it is difficult to detect the telltale irregularities which need to be observed during morphological screening and testing. The disclosed procedure overcomes the inadequacies of the traditional methods and stain techniques by permitting a uniformly thinner section to be cut from easily manipulated paraffin blocks and thus effecting a more penetrating stain.

An acceptable silver stain solution was prepared by dissolving 20 grams of silver nitrate in 100 cc of distilled water. Twenty-five cc of this 20% silver nitrate solution were mixed with 50 cc of a saturated lithium carbonate solution. Then 250 cc of distilled water were added and the silver carbonate was allowed to form a yellow-white precipitate. The clear supernatant was extracted and discarded, and 45 drops of a 28% ammonia water solution were added to the precipitate. The addition of the ammonia water results in the formation of a silver diamine complex.

The following study describes HCM in pigs and suggests that the existence of the porcine condition may prove to be an important model for the investigation of human cardiomyopathies.

The study population consisted of 131 purebred pigs and 64 hybrid pigs. The pigs came from the Boar Testing Station, the Pig Research Institute and the Nuclear Breeding Center of North Taiwan. They were necropsied between December 1990 and December 1992. HCM was diagnosed in 55 of the 131 purebred pigs; 46 of the 76 purebred pigs and 64 hybrid pigs without HCH were studied for comparative purposes.

After the entire heart was separated from the lung, removed from the thoracic cavity, and washed free of blood, it was fixed in 10% buffered formalin for 7 days. Ventricular slice, inflow and outflow and four-chambered dissections were employed for gross examination of the heart. Transmural sections were taken perpendicular to the long axis of the left ventricle from (i) the ventricular septum, the area of maximal thickening, approximately one-third the distance between the aortic valve and the left ventricular apex; (ii) the posterior left ventricular wall, approximately one-half the distance between the mitral valve annulus and left ventricular apex; and (iii) the anterior left ventricular wall, approximately 2 cm lateral to the anterior descending coronary artery.

After fixation in the 10% buffered formalin, tissue from the heart was taken and washed in running water for time periods ranging from 3 to 24 hours. The washed tissue sections were then dehydrated by soaking in an 80% alcohol solution for 2 hours and repeated with a fresh solution of 80% alcohol for a period of 1 hour. The dehydration was continued using a 95% alcohol solution. The tissue was soaked in two changes of 95% alcohol for periods of 1–2 hours each. Finally, the tissues were soaked in absolute alcohol for 3 changes of of 1–2 hours each. The tissue sections were then treated and cleared with two changes of xylene, each clearing\soaking lasting for 1–2 hours each. The tissue sections were then embedded with melted paraffin. The tissues were soaked in 3 changes of melted paraffin, Each soaking lasted 1–2 hours each. These soakings allowed the paraffin to penetrate deep into the cellular structure of the tissue. The paraffin embedded tissue sections were then allowed to cool quickly to form paraffin blocks. Histological sections, ranging in thickness from 25 to 30 microns each were cut from the paraffin blocks. The sections were deparaffinized in a 50 degree C. oven for 10 minutes, placed in xylene and shaken for 30–40 minutes. Sections were then rinsed in 3 changes of xylene for 2 minutes each. The sections were then rehydrated through soakings in 100%, 100%, 95%, 90% and 80% alcohol for 1 minute each. Sections were then washed in distilled water.

Washed sections were then stained a in silver stain solution at 60–62 degrees C. for 20 minutes and shaken in ammonia solution for 2 minutes. The sections were washed in distilled water 3 times for 1 minute each. After washing, the sections underwent reduction by dipping in 0.5% buffered formalin for 1 minute and washed in distilled water 3 times for 1 minute each. During the reduction, the silver diamine complex is reduced to visible metallic silver on those tissue structures that have been selectively impregnated with the silver diamine complex. Next, the sections were toned by dipping in 0.2% gold chloride for 1 minute, and rinsed in water. The metallic silver, visible as a result of the reduction process may appear brown or black depending on the amount of silver present or the particle size. These black-brown deposits may be transformed ("toned") into purple-black deposits of metallic gold by treatment with yellow or brown gold chloride. The metallic silver is oxidized to silver ions and the gold chlorideid reduced to metallic gold. Sections were dehydrated by soaking in 95% alcohol with 2 changes of two minutes each, 2 changes of 100% alcohol for 2 minutes each and clearing with 2 changes of xylene for 5 minutes. The sections were mounted with cytoseal, a xylene-based mounting medium, and examined microscopically.

The silver-impregnated HCM specimens showed marked increases in all components (coils, struts and weaves) of the matrix, as well as evidence of matrix disorganization. Matrix condensation was appreciated in areas of interstitial, replacement and perivascular scarring. More specifically, histologic abnormalities of matrix connective tissue in myocardium with hypertrophic cardiomyopathy included dense matrix connective tissue, representing increased perimysial coils running in different directions and associated with disarray of myocytes; increased permysial coil and weave fibers of matrix connective tissue spaces between myocytes; and connective tissue whorl composed of stretched and coiled perimysial coils running in different directions. The straightened coils most likely reflect abnormal contractile forces in areas of myocyte disarray.

The unique staining and tissue preparation techniques employed in the foregoing study on pig cardiomyopathies merely exemplify one of the many aspects of the invention disclosed herein. The procedures and techniques of the instant invention can be used to similar benefit in the study of all types of mammalian tissues. It is expected that tissue sections from the lung, liver, kidney, brain and other vital organs will also be sectioned or biopsied and fixed, blocked, stained and examined in the same manner as the cardiac tissue of the pigs in the above-described study.

The fixing of the tissues in formalin is also not crucial to the success of the disclosed and claimed procedures. Formalin is merely the most common fixative and any of a variety of preservatives would perform just as well.

Dehydration and rehydration of the tissue specimen need not be performed in the ritualistic manner demonstrated in the above-described experimental. A suitable number of dehydrations in a variety of alcohols would certainly work as well as the explicitly defined procedure set forth above, and anyone skilled in the art could be expected to effect suitable dehydration and rehydration of the specimen. It is certainly to be expected that any of the common aliphatic alcohols in any of the commonly available strengths would be suitable to vary the amount of water in the tissue being examined.

The use of xylene to clear the dehydrated tissue section is not critical to the success of the staining procedure. A variety of fat soluble, aromatic organic compounds would do an acceptable job in removing any excess fat from the tissue section.

Similarly, the use of any particular paraffin is not mandated to assure the technical success of the disclosed procedure. Any of a variety of paraffin waxes having suitable melting points, around 55 degrees C., would perform adequately to penetrate the collagen matrix and support the integrity of the tissue section.

Also, the deparaffinizing step can be accomplished in a variety of ways. Heating in an oven is recommended because of availability and ease of operation.

What is claimed is:

1. A method of identifying cardiovascular dysfunction in a mammal which comprises: fixing a cardiac tissue specimen from said mammal in a fixative solution, washing said specimen in water to remove excess fixative, dehydrating said washed specimen in an alcohol, clearing said dehydrated specimen with an aromatic organic compound, embedding said cleared specimen in a melted paraffin, allowing the embedded section to cool and form a paraffin block, cutting a histological section from 25 to 30 microns thick from said paraffin block, deparaffinizing said section, clearing said deparaffinized section with an aromatic organic compound, rehydrating said cleared section in an alcohol, staining said rehydrated section with a silver solution, dehydrating said stained section with an alcohol, clearing said dehydrated stained section with an aromatic organic compound, mounting the cleared section, and examining microscopically said stained section to detect any connective tissue abnormalities.

2. The method according to claim 1 wherein the fixative solution is formalin.

3. The method according to claim 1 wherein the aromatic organic compound is xylene.

4. The method according to claim 1 wherein the deparaffinizing procedure is conducted in an oven.

5. A method of fixing and staining a mammalian cardiac tissue specimen which comprises: soaking said tissue specimen in a fixative solution, washing said specimen in water to remove excess fixative, dehydrating said washed specimen in an alcohol, clearing said dehydrated specimen with an aromatic organic compound, embedding said cleared specimen in a melted paraffin, allowing the embedded section to cool and form a paraffin block, cutting a histological section from 25 to 30 microns thick from said paraffin block, deparaffinizing said section, clearing said deparaffinized section with an aromatic organic compound, rehydrating the cleared section in an alcohol, staining said rehydrated section with a silver solution, dehydrating said stained section with alcohol and clearing said dehydrated section with an aromatic organic compound.

6. A chemically fixed silver stained mammalian cardiac tissue section from 25 to 30 microns thick prepared according to the method of claim 5.

\* \* \* \* \*